United States Patent [19]
Parra

[11] Patent Number: 5,255,685
[45] Date of Patent: Oct. 26, 1993

[54] ACOUSTIC DIAGNOSTIC APPARATUS WITH SCAN CONTROL

[76] Inventor: Jorge M. Parra, 7332 Grand Blvd., New Port Richey, Fla. 34652

[21] Appl. No.: 766,247

[22] Filed: Sep. 27, 1991

Related U.S. Application Data

[63] Continuation-in-part of Ser. No. 588,985, Sep. 26, 1990, Pat. No. 5,137,029, and a continuation-in-part of Ser. No. 569,121, Aug. 17, 1990, Pat. No. 5,031,637.

[51] Int. Cl.$^5$ .............................................. B61B 7/02
[52] U.S. Cl. .................................... 128/670; 128/773
[58] Field of Search ...................... 128/773, 782, 653.1, 128/660.07, 668, 691, 670; 73/613; 367/901, 122

[56] References Cited

U.S. PATENT DOCUMENTS

| | | | |
|---|---|---|---|
| 3,269,173 | 8/1966 | Arderre | 128/660.07 |
| 3,778,756 | 12/1973 | Houston et al. | 128/660.07 |
| 4,763,661 | 8/1988 | Sommer et al. | 128/660.07 |
| 5,031,637 | 7/1991 | Parra | 128/773 |
| 5,115,813 | 5/1992 | Ylander et al. | 128/660.01 |
| 5,137,029 | 8/1992 | Parra | 128/773 |

Primary Examiner—Lee S. Cohen
Assistant Examiner—Robert L. Nasser, Jr.
Attorney, Agent, or Firm—Jim Zegeer

[57] ABSTRACT

An acoustic diagnostic apparatus has a vessel for containing at least a portion of a body of an human or other animal and a wall surface carrying a plurality of transducers, the outputs of which are examined in via a scanning system controlled by a microprocessor which allows primary path acoustic signals to be selected over secondary acoustic path signals to enhance detection of the body's acoustic signals for diagnosis.

4 Claims, 6 Drawing Sheets

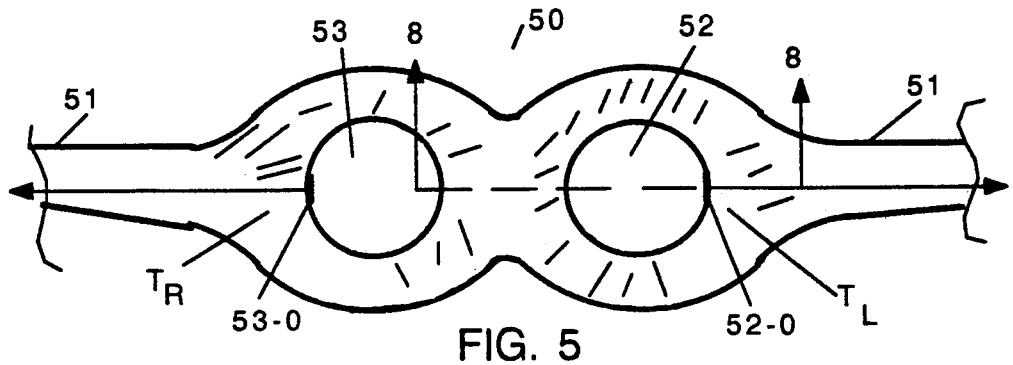
FIG. 5
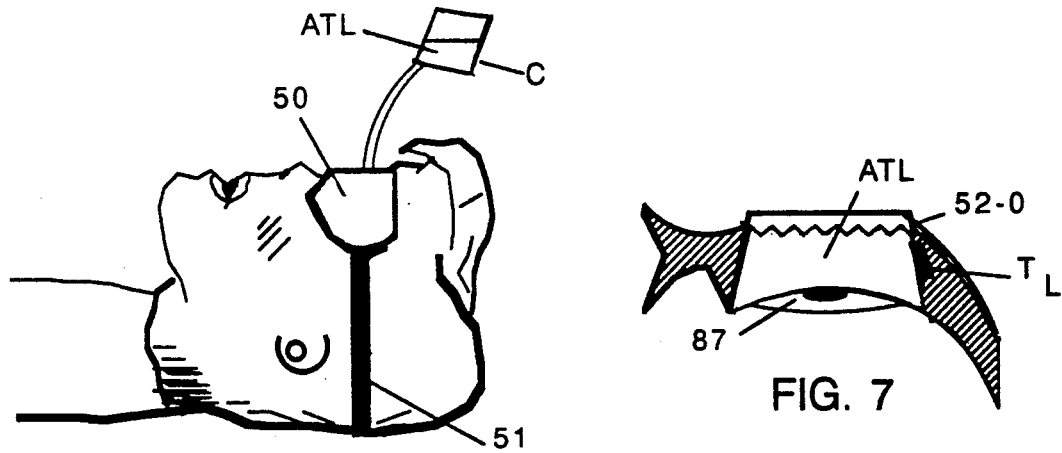
FIG. 6
FIG. 7
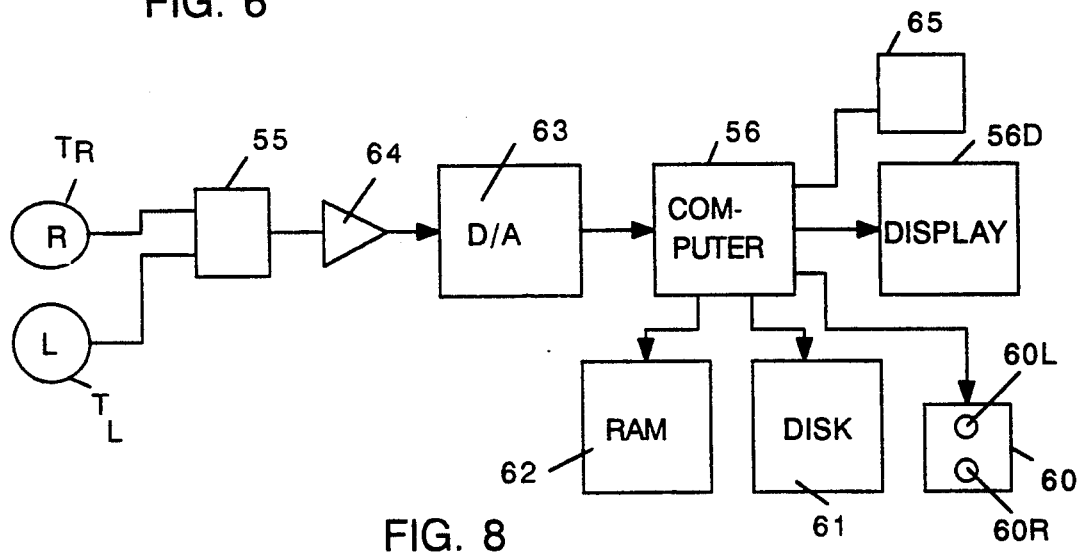
FIG. 8

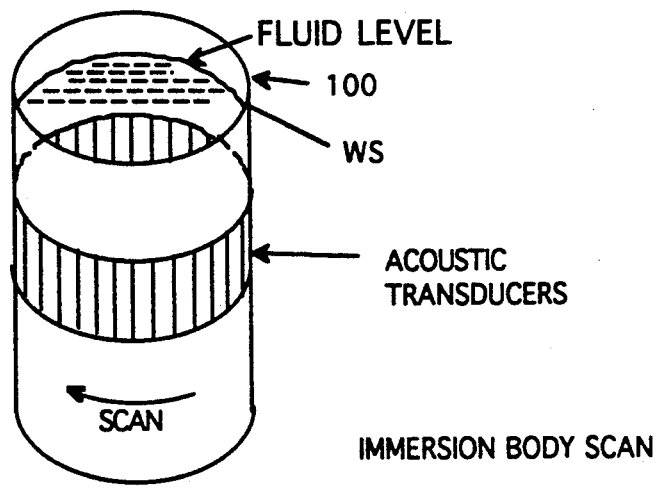
IMMERSION BODY SCAN
FIG 13a
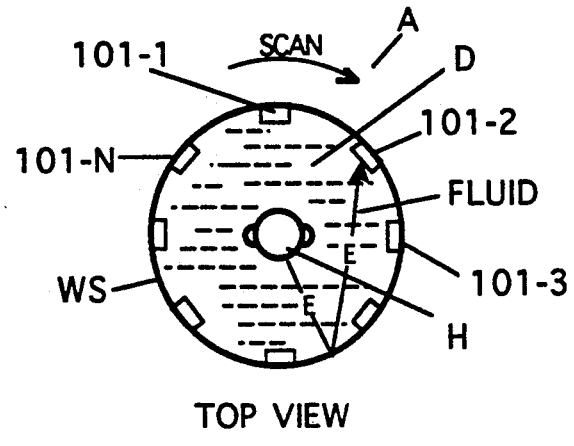
TOP VIEW
FIG. 13b
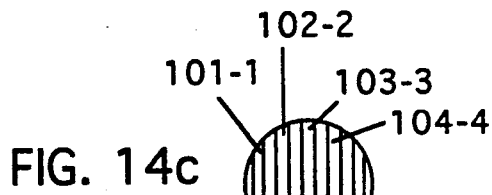
FIG. 14c
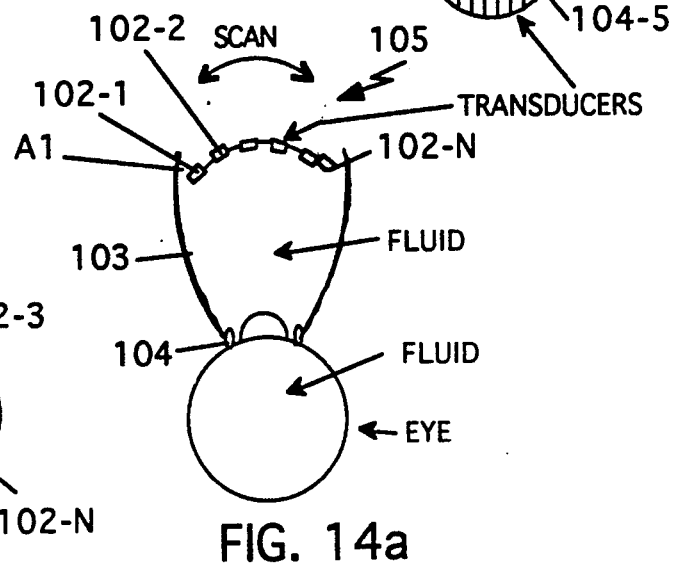
FIG. 14b
FIG. 14a SPEED OF THE SCANNING IS VERY SIGNIFICANT FOR WAVE ISOLATION AND DETAIL-
ALSO ADDS ERASING CAPABILITIES TO UNDESIRED WAVE FORMS.

ACOUSTIC DIAGNOSTIC APPARATUS WITH SCAN CONTROL

REFERENCE TO RELATED APPLICATIONS

This invention is a continuation-in-part of my application Ser. No. 07/588,985, filed Sep. 26, 1990 for "NON-INVASIVE OPHTHALMIC DIAGNOSTIC METHOD AND APPARATUS", new U.S. Pat. Nos. 5,137,029, and 5,031,637, issued Jul. 16, 1991.

BACKGROUND OF THE INVENTION

Stethoscopes and like apparatus have been used for many years to listen to sounds made by the human body and to make diagnostic analysis of various conditions in the human body. The sounds produced are typically in the sonic range and while stethoscopes are, obviously, widely used by the medical profession, the types of analysis and uses for such apparatus is relatively limited primarily to the chest cavity area (e.g., breathing and gas flow in the lungs, etc.) and for blood pressure readings in the cardiovascular system.

My above-identified U.S. Pat. No. 5,031,637 is directed to a non-invasive diagnostic apparatus and method wherein the human body or a portion thereof is placed in a body of an acoustically transmissive liquid, such body of acoustically transmitting liquid being contained in a container preferably having sidewalls formed of or coated with acoustically absorbent material. One or more hydrophones are located in the body of liquid to detect or "listen" to sounds, such as cardiovascular sounds, gas flow and skeletal sounds made by body movements. These sounds are passed through a preamplifier, a bandpass filter and discriminator, the function of which may be performed by microprocessors to a recorder and/or display device. The recorder can record body sounds much in the fashion of an strip chart recorder used for EKG and/or EEG. Typical pool water with chlorine, or salt water, or oils, such as vegetable oils can be used for the acoustically transmissive medium. In addition to audible sounds, the method and apparatus are particularly useful for listening to infrasonic or subsonic sounds. According to my above application, the subject is placed or immersed in the body of acoustically transmissive liquid in a container having acoustically absorbing walls so that there are no unwanted reflections of sounds launched in the water from the human body reflecting off of the walls. One or more hydrophones located in the body of water are used to detect the sonic energy launched by the human body. The human in the body of acoustic liquid is instructed to go through a particular sequence of movement, for example, the arms, (flexion, extension, abduction, adduction), or the back, or legs (inversion eversion), etc. and record is made the sounds emitted during each of the movements of the specific body parts or the specific movement made by a given patient. For example, an athlete may be asked to bend his or her knee (flexion, extension), elbow (flexion, extension) and the like and a record is made of the sounds generated and launched into the acoustically transmissive liquid. Similar recordings are made for a large number of individuals to provide a norm of the movements of a particular body part in a particular direction and/or at a particular rate of speed. These records then form a database which may be stored in the computer database and used to detect departures from the normal sounds made and thereby provide the physician with a greater body of knowledge to enable successful treatment for the patient.

THE PRESENT INVENTION

The present invention relates to the scanning of a plurality of transducers when a body or portion thereof is immersed in an ATL contained in a vessel. The transducers are scanned and the speed of the scanner allows primary path biosounds to be selected to a selected transducer thus enhancing it over the secondary or tertiary path or paths and received signal from unscanned transducers.

In my above application Ser. No. 07/588,985, sound made by the flow of blood in the retinal blood vessel system of the human eye which, when the exposed portion thereof is partially or completely immersed in a body of acoustically transmissive liquid (ATL), are directly coupled and launched into the acoustically transmitted liquid. A plurality of transducers are mounted in the ATL and coupled to electronic processing systems for diagnosis and display. Piezo plastics (PVF$_2$, for example) having a flat frequency response in the infrasonic range are preferred. The blood vessel system of the human eye has a unique acoustic signature in the infrasonic range. Injured or diseased eyes or eyes reflecting muscular degeneration have unique acoustic signatures e.g., sounds they make, which are launched into the ATL and thus each individual retinal blood flow system make or produce a unique pattern of noise or sounds which are normally inaudible, but when immersed in a body of water or neutral eye wash liquid, can be detected by hydrophones or underwater microphones. The invention has use in medical diagnosis of eye ailments as well as providing a baseline for future diagnosis of human eyes.

The present invention provides for control of the speed of scanning for wave isolation and detail enhancement and adds erasing capabilities to undesired waveforms.

BRIEF DESCRIPTION OF THE DRAWINGS

The above and other objects, advantages and features of the invention will become more apparent when considered with the following specification and accompanying drawings wherein:

FIG. 5 is a partial top view of the ATL reservoir according to the invention, FIG. 6 is a side elevational view of a patient with the ATL reservoirs, FIG. 7 is a partial sectional view taken on lines 7—7 of FIG. 6, FIG. 8 is a block diagram of a circuit incorporating the invention, FIGS. 13a is a perspective view of an immersion body scan apparatus, and FIG. 13b is a top plan view thereof indicating the direction of scan, FIGS. 14a, b,and c as a diagrammatic illustration of the scanning transducer for ophthalmic purposes, FIGS. 15a diagrammatically illustrates the scanning time interval of each transducer can be varied as well as the scanning speed.

DETAILED DESCRIPTION OF THE INVENTION

Figure 1:
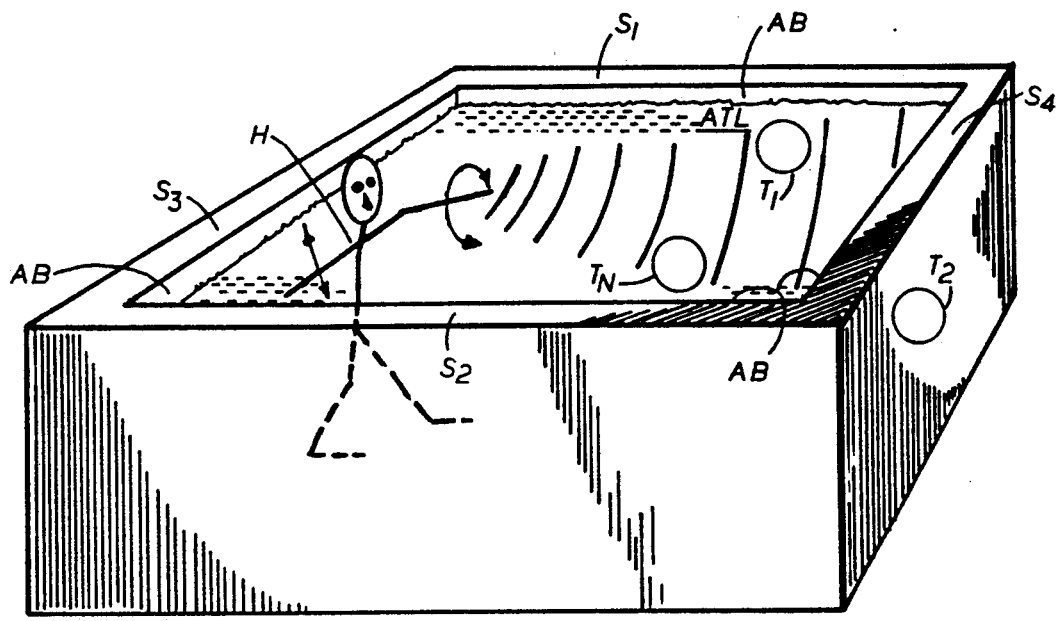
FIG. 1 is a perspective isometric view of the apparatus disclosed in my above-identified U.S. Pat. No. 5,031,637.

Referring to FIG. 1, a vessel or container 10 which is of sufficient size to at least hold a portion of a human body therein such that the portion can be voluntarily articulated by the human without engaging or contacting the sidewalls. In the illustrated embodiment, the vessel 10 is a large tank in which a human H is immersed up to the neck line. In a preferred embodiment, the sidewalls S1, S2, S3 and S4 and bottom are preferably formed of or coated with an acoustic absorber AB so that there are substantially no reflections of acoustic energy from the sidewalls and that any acoustic energy launched by the human H body, or body parts, are received directly by one or more hydrophones T1, T2...TN, which are oriented to face the human's body. (While the specimen or patient is a human, it will be appreciated that the same techniques may be used in connection with race horses, dogs, cats and other animals, but, in this preferred embodiment, the invention is particularly applicable to diagnostic purposes for use with humans).

Figure 2:
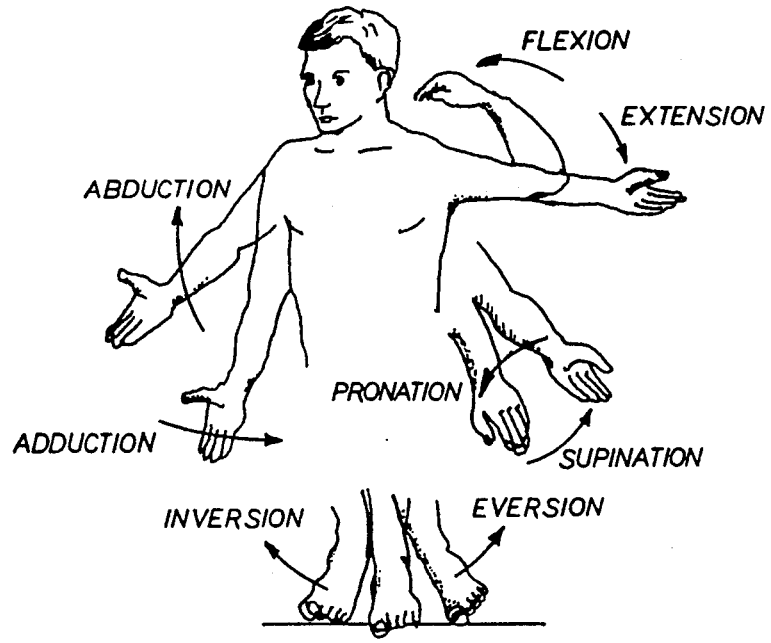
FIG. 2 is a diagrammatic illustration of a few movements of the body at the joints (from Wedding et al. "Medical Terminology", copyright 1988)

Various movements made by the body at the joints are illustrated in FIG. 2 and these generate sounds. According to the invention, sounds emitted from the human body caused by movements of the skeletal portion (skeletal sounds) and/or blood flow (cardiovascular sounds) and/or air flow are detectable using the invention.

Noises made by the flow of blood in the human cardiovascular system and skeletal noises in the joints of a human skeleton provide a wide variety of sounds (mostly infrasonic) which, when the human body is partially or completely immersed in a body of an acoustically transmissive liquid medium ATL such as water, vegetable oil, etc., are directly coupled to the liquid medium and thus launched into the liquid medium. Each joint, for example, has a unique acoustic signature. Joints which are injured or diseased can have their own unique acoustic signatures or sounds they make which are launched into the liquid medium. Thus, each individual skeletal system makes or produces a unique pattern of sonic energy or noise which are normally infrasonic or but, when immersed in a body of acoustically transmissive liquid such as water, vegetable oil and the like, can be detected by hydrophones or underwater microphones T1, T2 . . . TN.

In FIG. 1, the hydrophone or transducers T1, T2 . . . TN may comprise of one or a plurality of different microphones, and are each referred to herein as acoustic transducers and they convert acoustic energy transmitted in the body of acoustically transmissive liquid ATL.

Acoustic transducers T may be positioned in the body of acoustically transmissive liquid ATL or a wall of vessel 10 and converts all sonic energy to electrical signals. As shown in the block diagram of FIG. 3, the electrical signals produced by transducer T2 are amplified by preamplifier 12 and supplied to a bandpass filter 13, the output of which is supplied to a discriminator 14 and then to a display or recorder 11. The bandpass filter removes unwanted background noise and interference and passes the desired cardiovascular and/or skeletal sounds. The configuration of the filter is in a cascaded high-pass/low-pass configuration to maximize attenuation outside the desired frequency. While there are some sounds that are in the audible range, typical sounds made by the movement of the human skeletal system are in the subsonic or infrasonic range and thus in the preferred embodiment, the bandpass filter is designed to restrict frequencies to this. Moreover, the solid state discriminators include a phase lock loop PLL which is adjustable or programmed by adjustable resistor R1 to pass a predetermined discrete pattern of electrical signals constituting a sonic profile, signature or imprint of the movement of a selected body part. For example, the up and down sidewise movement (abduction-adduction) of the human arms shown in FIG. 1 is movement of the humerus bone or upper arm bone in the shoulder, movement of the fibial relative to the femur e.g., the knee joint, provides subsonic sounds (apart from the audible snapping of joints) which are unique and distinctive.

Figure 4:
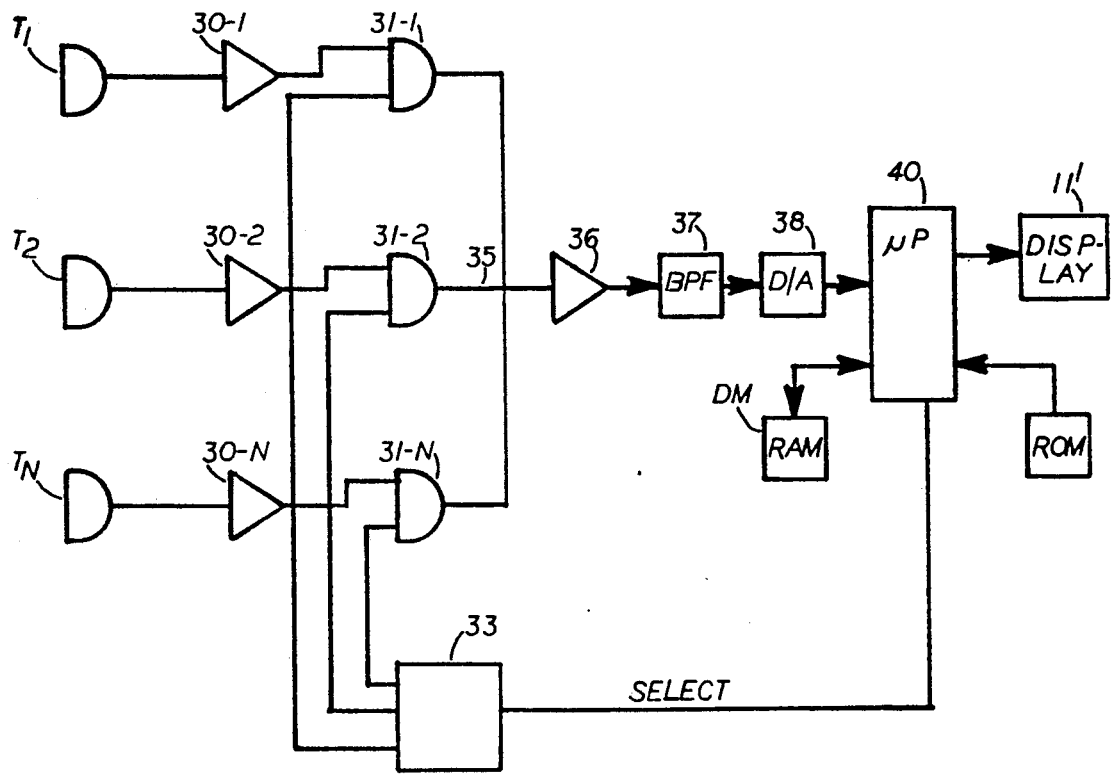
FIG. 4 is a detailed block diagram.

Referring now to in FIG. 4, a plurality of transducers T1, T2 . . . TN have their outputs amplified in preamplifiers 30-1, 30-2 . . . 30-N. While the multiplexing operation can be performed either at the transducer head or in an electronic's compartment, in this embodiment, the multiplexing operation is performed at the transducer head. In this case, the gates 31-1, 31-2 . . . 31-N receive gate signals from counter 33 via line "select". The gated analog signals are coupled by a coaxial cable 25 to an amplifier 36, bandpass filter 37BPF and analog-to-digital converter 38. The digital signals constituting the multiplexed output for the individual transducers are then supplied to the microprocessor 40 which controls the "select" line and, in turn, the counter 33.

In this case, the microprocessor 40 performs the filter and discriminator functions discussed earlier, to identify and classify the acoustic signatures from the different body systems, and also operates the display 71 which may be a CRT, LCD, plasma, or EL display.

In addition, a read-only memory ROM is provided for storing sonic profiles of large number of joints or cardiovascular flow in particular parts of the body which is used to compare with the incoming acoustic or sonic profiles so as to identify the sounds and the cardiovascular or skeletal system from which they emanate. At the same time, microprocessor 40 stores for short term use data in a random access memory DM.

The entire spectrum of sonic signals for each joint in the skeletal system or the cardiovascular system and each part of the body may be detected, digitized and stored in a computer memory. For this purpose, a digital-to-analog converter DA is provided for converting each acoustic signature to a digital signal and processed by microprocessor MP and stored in a digital memory DM. Moreover, each acoustic signature may be analyzed and compared with a standard acoustic signature which has been derived from analysis of a large number of acoustic signatures. For example, a large number of individuals may be placed in vessel 10, and asked to move a particular part of their body in a particular fashion. For example, the human H shown in FIG. 1 is asked to point his right arm directly outwardly from the side and then move it in an arc up and down (while the shoulder joint is, of course, below the surface of the acoustically transmissive liquid ATL). See FIG. 2 for a sample of the various movements. A large number of individuals are asked to do the same articulation of their right arm. The acoustically recorded signatures for each individual are then analyzed to establish a norm or "standard" which may be stored in a read only memory ROM, along with other fixed program files. The standard may be according to age, sex, physical size (e.g., skeletal size). As another example, a group of individuals may each be asked individually to insert their leg into the acoustic transmissive liquid ATL and hold it stationary and the transducer 11 used to detect the infra subsonic signals made by the coursing of the blood flow through the cardiovascular system and thereby derive an acoustic signature to establish as a standard comparison. In like manner, individuals having a particular ailment may be asked to immerse a part of their body into the acoustically transmissive liquid and those known ailments then utilized as a base for establishing a characteristic departure from the standard. Numerous other examples of similar character may be given but it is believed that the above is sufficient to establish the broad implication and applications of the invention.

Since the acoustic signatures for different skeletal areas and parts of the human and flows in different parts of the cardiovascular system have their own characteristic acoustic signatures, transducers may constituted by a plurality of hydrophones T1, T2 ... TN for example, and bandpass filters, one utilized for example, for selected cardiovascular signals and one used for selected skeletal signals. Large numbers of individual channels may be utilized, each attuned to a particular skeletal sound or a particular cardiovascular sound. Finally, different combinations of skeletal and cardiovascular sounds may be utilized to detect and identify a particular individual or to detect and identify particular ailments and/or symptoms of ailments.

Referring to FIG. 6, a separate acoustically transmissive liquid reservoir is provided for each eye by swimmer-like goggles 50 which is formed of soft flexible elastomeric material so as to closely conform to and be shaped by skin, tissue and bone structures surrounding each eye cavity. Because it is made of a soft form-retaining material, it serves as an acoustic absorber and acoustic reflections are eliminated or minimized. An elastic headband 51 draws each conforming structure 52, 53 into a snug and sealing engagement with each eye cavity so that the reservoirs 52 and 53 can be filled with acoustically transmissive liquid from container C. Although the reservoirs are shown as circular, they could just as well be square.

The inner wall surfaces of the reservoirs are treated with acoustically absorbent material, but the small size of the reservoirs and soft rubber and the low frequency of interest assure that there are little or no reflections. Transducers $T_R$ and $T_L$ and are mounted in the outside sidewalls 52-0 and 53-0, and are preferably hydrophones made of piezoelectric plastic (such $PVF_2$ polarized homopolymer of vinylidene fluoride (PVDF)) materials which are well known in the art. One commercial source of these materials is Pennwalt Corporation of Pennsylvania under their $Kynar_R$ brand pizeo plastic.

Figure 3:
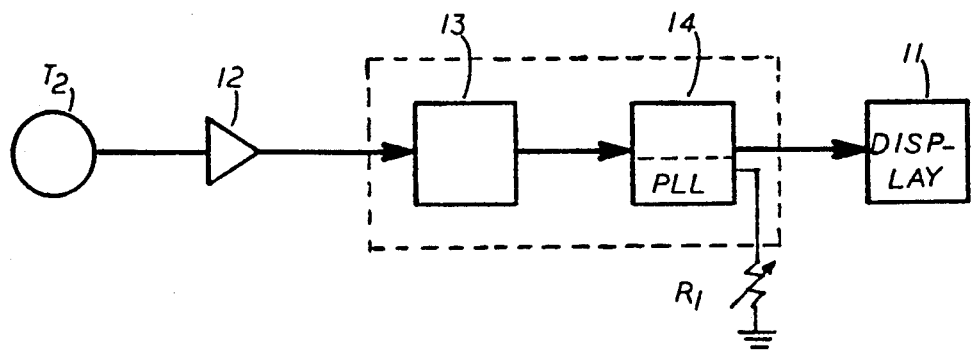
FIG. 3 is a simplified block diagram.

The transducers are connected to the circuit shown in FIG. 3 which has been tuned for ophthalmic frequencies and acoustic patterns. These materials are preferred because of their good (flat) response in the low infrasonic range for retinal blood flow analysis.

Figure 9:
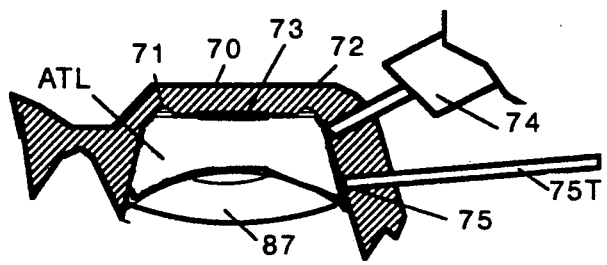
FIG. 9 is a sectional view of a further embodiment of the ATL reservoir and transducer.

Referring to FIG. 9, alternatively, the transducers $T_R$ and $T_L$ convert sonic energy in the ATL in each reservoir 52, 53 are electrically connected to a computer controlled selector switch 55. Although parallel channels (of FIG. 3 type) could be used for signal processing, the arrangement shown in FIG. 9 is preferred. Computer 56 controls the operation of selector switch 55 so that alternate ones of transducers $T_R$ and $T_L$ are connected to the processing system. A selector switch 60 may be provided so that an operator can select 60R or 60L to select the left or right eye for examination and analysis.

To establish a library of ophthalmic acoustical signatures, a large number of eyes are acoustically examined and their infrasonic signatures recorded with the apparatus of FIG. 9. Acoustic signatures of a large number of healthy eyes are analyzed to form a composite or standard acoustic signature for healthy eyes and stored in memory RAM or ROM. Likewise, the acoustic signature of a large number of eyes having various eye ailments ranging from various retinal disorders such as retinal detachment, bleeding, loss of or reduced blood flow, etc., incipient problems related to small hemorrhaging that do not go into the eye fluid and similar problems where low level sound generally in the infrasonic range is generated, are detected and stored in a memory 61 disc (magnetic or optical), tape or in a chip (ROM). RAM 62 may be used to store current acoustic signals and signatures of the patient being examined. The front end of computer 56 includes a digital-to-analog converter 63, a preamplifier 64.

In a preferred embodiment of the invention, the signal is bandpass filtered and this can be done prior to the digital-to-analog conversion or in the computer 56. It will be appreciated that the infrasonic signals can also be processed on a purely analog basis as in FIG. 3. Since most of the signals of interest are in the infrasonic range (e.g., under about 15 Hz), they are preferably multiplied to a higher frequency range for easier processing and this can be done electronically in computer 56 or mechanically (e.g., a magnetically taped infrasonic recording is run at a higher speed (e.g. 5X–10X) during playback) to produce audible versions of the acoustic signature.

The heart beat of the subject can be detected by transducer 65, and an electrical signal corresponding to heart beat can be supplied to computer 56 for correlation with the infrasonic signals from transducers $T_R$ and $T_L$ and thus provide further diagnostic information for eye problems. In case of FIGS. 1-6, the heart beat signal can also be used to enhance the diagnostic process.

Figure 10:
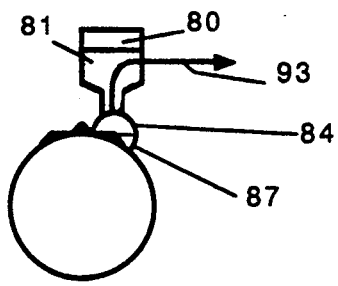
FIG. 10 illustrates a commercial eye cup eyewash container equipped with a transducer on the head of a patient or subject.

In FIGS. 7 and 8, the ATL reservoir is used when the subject or patient is in a prone or lying position. However, in order to take readings of the eye when the patient is standing or lying down, the embodiment of FIG. 10 is provided. In FIG. 10, a cover panel 70 is integrally formed or molded with the goggle eye pieces or reservoirs 52, 53 and is, in a preferred embodiment, provided with an annular groove 71 surrounding a transducer pedestal 72 carrying transducer 73. A syringe-like tool 74 is used to inject ATL into reservoir and/or air vent 75 on the forehead eyebrow end of the goggles when the liquid reaches the vent and starts to flow out, all air bubbles which could muffle or attenuate coupling of acoustic signals to the transducer are eliminated. The vent may be with a small transparent tube 75T as an indicator that the reservoir is full.

Figure 11:
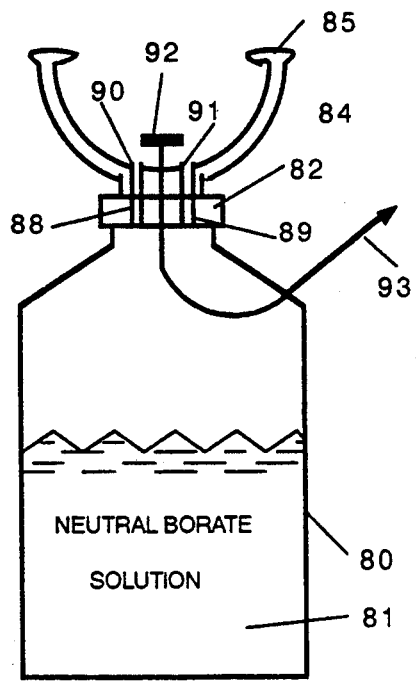
FIG. 11 is a sectional view of the eye cup eyewash container shown in FIG. 10.
Figure 12:
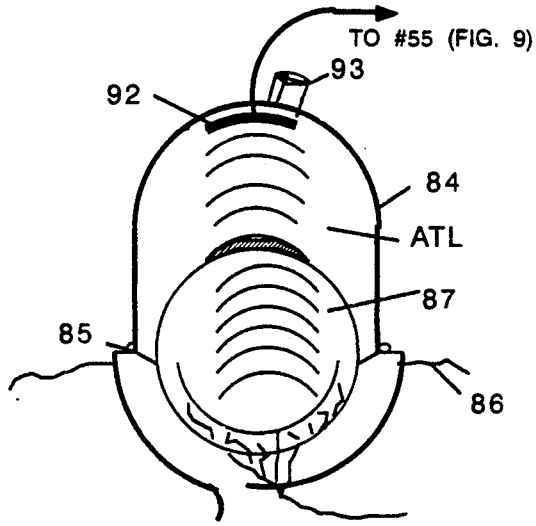
FIG. 12 illustrates the eye cup and transducer assembly on an eye.

In another embodiment of the invention shown in FIGS. 11, 12 and 13, a commercial eye cup/container 80 containing a commercial eye wash solution 81, which in this embodiment is a neutral borate solution, as the ATL, has a cover 82 carrying eye cup 84 with an annular ring 85 for sealing engagement with the tissue structures 86 surrounding the eye 87. According to the invention, cover 82 is provided a plurality of holes or openings 88, 89 which communicate with holes or openings 90, 91 in eye cup 84 to allow ATL liquid to flow freely into the eye cup when the container 80 is inverted. An acoustic transducer 92 is acoustically coupled by the ATL to the blood vessels in the eye. An interconnecting cable 93 carries the electrical signals produced by the transducer to the processing unit for display such as display 11 (FIG. 3) or 56D (FIG. 9). In FIG. 13, the eye cup is filled through a filler lock 93 by means of a syringe-like device 74 shown in FIG. 10.

In the preferred embodiment, the quantity of fluid in the reservoir is insufficient to place any significant pressure on the eye. In the preferred embodiment, the ATL is over the entire exposed surface so that a good acoustic couple is achieved. Moreover, even when the eyelid is closed, a good acoustic couple is achieved. However, in this case, the retinal acoustic signals are stronger than those of the eyelid and care must be taken to discriminate between the two. It is preferred that for retinal blood flow, studies and diagnosis, the eyelid should be open to avoid detecting acoustic signals due to blood flow in the eyelid structures.

Referring to FIG. 13, a circular or closed wall having an end surface WS, body immersion vessel 100 is filled to a level L with an acoustic transmissive liquid ATL and a plurality of transducers 101-1, 101-2, 101-3, 101-4 ... 101-N in a circular array on the interior walls of immersion body scan vessel 100. The transducers 101 may overlap or be slightly spaced an arc distance D. Moreover, the transducer may be of different arc lengths, but preferably are of the same arc length. As shown in FIG. 13b, eight equal transducers are spaced on equal arc distances in the ATL vessel 100.

In FIG. 14, an eye cup or eye ATL vessel 103 includes an arcuate transducer carrier or support 102 which is secured to the outer interior wall edges of ATL vessel 103 by acoustic insulator AI, which may be a sponge or foam ring. The inner wall edges have a seal sponge or foam member 104 secured thereto to prevent leaking of ATL fluid during the examination. Transducer assembly 105 includes a plurality of transducers 102-1, 102-2, 102-3...102-N which are maintained in a matrix array or pattern in arcuate or curved transducer carrier or support 102 which is acoustically isolatingly supported by ring AI to dampen the effect of blood flow in veins and arteries surrounding the eyeball E. Normally, eye fluid fill the eyeball and transmit acoustic information which is coupled to the ATL as described earlier.

Figure 15A:
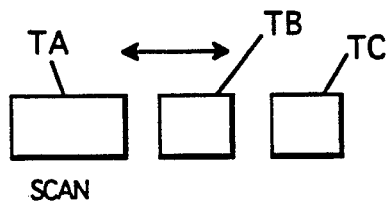
FIG. 15b is a schematic block diagram of the invention for controlling the speed of scan to achieve wave isolation and enhance the diagnosis.
Figure 15B:
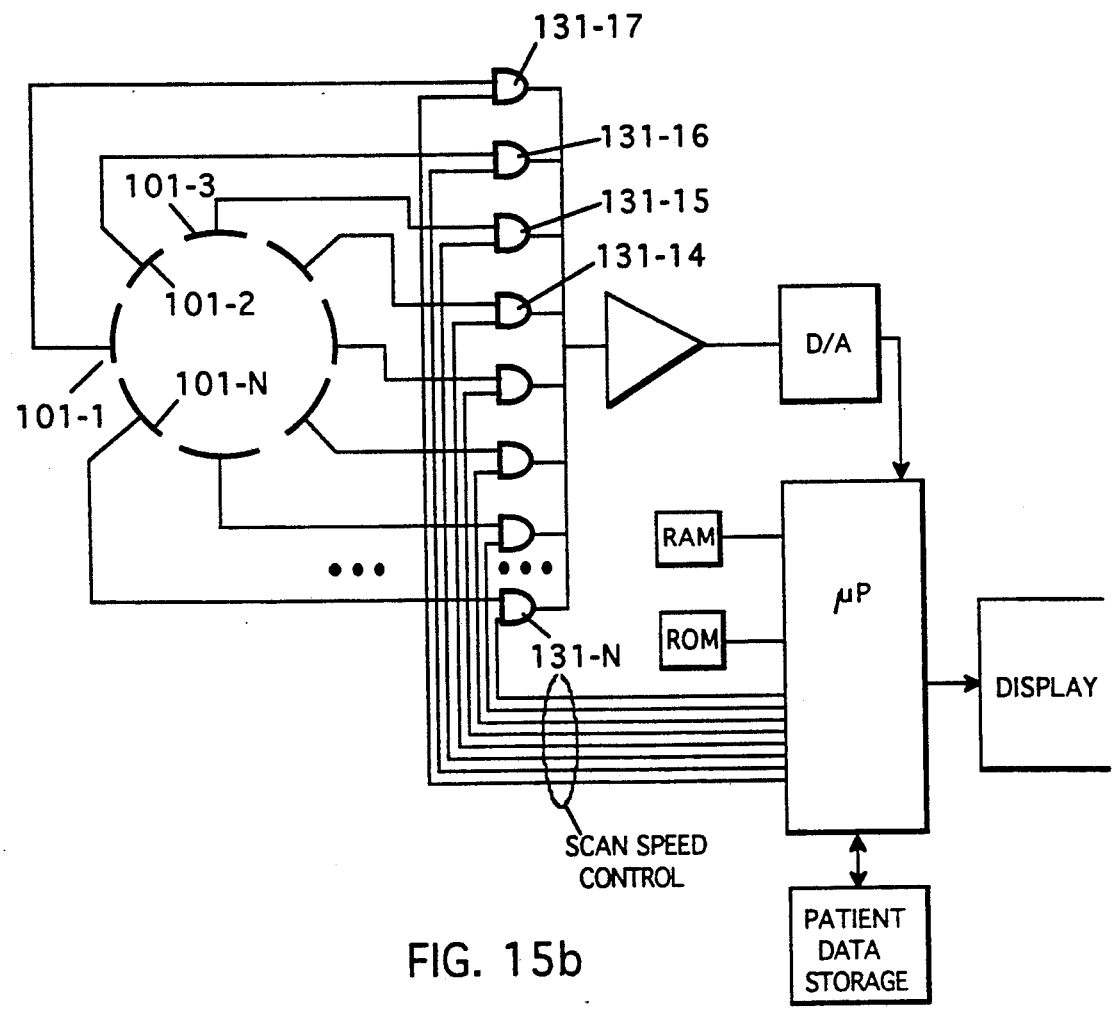

FIG. 15b is similar to FIG. 4, with a larger number of acoustic transducers and it will be appreciated that the transducers may be arrayed for immersion body scan as shown in FIGS. 13a and 13b or smaller transducer segments in a matrix array as shown in FIGS. 14a and 14b or strips as in FIG. 14c. The transducers in this embodiment can be small plastic $PVF_2$ patches (KYNAR ® by Pennwalt). Each transducer may have a preamplifier (not shown) associated therewith.

The scan speed, or alternatively the dwell time, on each transducer element is significant for wave isolation and enhancement of the acoustic detail from selected segments and also adds erasing capabilities to undesired waveforms. In FIG. 13b, 11 is the biosound source, 101-1, 101-2, 101-3 ... 101-N are the acoustic transducers. The arrow A indicates the direction orientation or rotation of the scanners (it being appreciated that the direction of scan is arbitrary), C1 is the speed of rotation (angular). D is the primary acoustic path between source H and a given transducer, 101-2, for example, and E is the secondary path between the source H and transducer 101-2, for example. The ratio or speed of the scanner, when in the sequential scanning mode, allows primary path biosound to be selected to a certain transducer, thus enhancing it over the secondary and tertiary path and the received signal from unscanned transducers. When there are acoustic signals of interest detected at a pair of given transducers, the processor 40' causes the gates 131 for that transducer to remain open for a longer period of time and even dwell on that transducer (FIG. 15a indicates a longer scan interval on transducer TA than on transducer TB and TC). If several transducers receive acoustic signals of interest, the microprocessor controls the gates 131 of those transducers and compares the acoustic signals from the two or more transducers to enhance the diagnostic process.

Moreover, adjacent or contiguous transducers can be considered as one and the gates 131 for contiguous transducers opened simultaneously. Thus, referring to FIG. 15b, gates 131-17 and 131-18 could be opened simultaneously so that acoustic signals transduced by transducer 101-1 and 101-2 are simultaneously processed by microprocessor 40', then gates 131-16 and 131-15 are simultaneously opened so that acoustic signals transduced by transducers 101-2 and 101-3 are simultaneously processed by microprocessor 40'. In this mode, the scan speed can be adjusted as discussed above. While only a single output channel is shown, if it is desirable to separate the data from contiguous transducers while their outputs are being simultaneously outputted by the respective gate circuits 131, a separate channel for each can be provided as shown in FIG. 3.

In FIG. 15b, the signal processing is essentially digital and by microprocessor 40' which performs the filtering sand discrimination function discussed above.

While there has been shown and described a preferred embodiment of the invention, it will be appreciated that various other adaptations and modifications of the invention will be readily apparent to those skilled in the art and it is intended to encompass such obvious modifications and adaptations in the spirit and scope of the claims appended hereto.

What is claimed is:

1. A non-invasive medical apparatus comprising:
    a vessel holding an acoustically transmissive liquid (ATL), said vessel being of sufficient size to hold at least a portion of the body of an animal therein such that said portion generates infrasonic acoustic signatures and launch same into said acoustically transmissive liquid,
    said vessel having a wall surface,
    a plurality of acoustic transducer means sequentially mounted on said wall surface and immersed in said body of acoustically transmissive liquid for converting said infrasonic acoustic energy travelling in said acoustically transmissive body of liquid to electrical signals, there being primary acoustic paths between said body and one or more of said transducer means and one or more secondary paths between said body and said one or more transducer means, means for scanning said acoustic transducers means, including electronic gate means, and a microprocessor means for controlling said gate means to allow the primary path acoustic signals to be selected over secondary path acoustic signals, means connectable to said transducer means for detecting the acoustic signatures of parts of said body.

2. The invention defined in claim 1, said means for detecting is said microprocessor means and including means for identifying the portion of the body from which said acoustic signature originates.

3. The invention defined in claim 2 including means for storing a standard acoustic signature for a selected skeletal and cardiovascular part, and comparing subsequent acoustic signatures with said selected standard acoustic signature.

4. The invention defined in claim 1 wherein said portion of the body is a human eyeball and said vessel includes means for holding said wall surface in space relation to said eyeball with said ATL filling the space therebetween.

* * * * *